United States Patent [19]
Greenwald et al.

[11] Patent Number: 5,621,330
[45] Date of Patent: Apr. 15, 1997

[54] DEVICE AND METHOD FOR DETERMINING THE MOISTURE CONTENT OF A BALE OF MATERIAL WITH MULTIPLE LAYERS

[75] Inventors: Alexander Greenwald, Nazareth-Illit; Danny S. Moshe, Kiryat Ono; Boris Tsentsiper, Jerusalem, all of Israel

[73] Assignee: Malcam Ltd., Nazareth Illit, Israel

[21] Appl. No.: 503,838

[22] Filed: Jul. 18, 1995

[51] Int. Cl.$^6$ ................................. G01N 22/04
[52] U.S. Cl. ..................... 324/640; 324/637; 324/639; 73/73
[58] Field of Search ................... 324/637, 639, 324/640; 73/73

[56] References Cited

U.S. PATENT DOCUMENTS

| | | | |
|---|---|---|---|
| 2,659,860 | 11/1953 | Breazeale | 324/640 |
| 3,360,721 | 12/1967 | Pullman | 324/640 |
| 3,644,826 | 2/1972 | Cornetet, Jr. | 324/640 X |
| 4,500,835 | 2/1985 | Heikkila | 324/637 X |
| 4,578,998 | 4/1986 | Gard | 73/73 |
| 4,675,595 | 6/1987 | Hane | 324/640 |
| 5,333,493 | 8/1994 | Cutmore | 324/640 X |

OTHER PUBLICATIONS

P.R. Ismatulayev et al., "Theoretical and Experimental Investigation of Microwave Moisture Measurement of Materials", FAN Uzbekistan, 1982 (month unavailable).
E.S. Krichevskii et al., "Monitoring of the Moisture Content in Solid and Incoherent Materials" (undated).

*Primary Examiner*—Kenneth A. Wieder
*Assistant Examiner*—Diep Do
*Attorney, Agent, or Firm*—Mark M. Friedman

[57] ABSTRACT

A system for measuring the moisture content of a multi-layer bale of material, comprising a source of microwave radiation disposed on a first side of the bale for directing a circularly polarized source beam through the bale in a direction substantially parallel to the layers thereof so as to exit from the bale as an exit beam and a conveyor for conveying the bale past the source of microwave radiation. A pair of microwave antennas are disposed on an opposite side of the bale for receiving mutually orthogonal components of the exit beam permitting determination of a maximum amplitude of the exit beam corresponding to an amplitude of the exit beam in a direction normal to the layers of the bale. This permits calculation of an attenuation of the beam consequent to absorption by moisture in the bale and thus allows the moisture content of the bale to be determined.

13 Claims, 6 Drawing Sheets

DEVICE AND METHOD FOR DETERMINING THE MOISTURE CONTENT OF A BALE OF MATERIAL WITH MULTIPLE LAYERS

FIELD OF THE INVENTION

This invention relates to a system for the measurement of moisture content of a material, particularly a multi-layer bale of cotton.

BACKGROUND OF THE INVENTION

During the processing of cotton gins are used for separating the cotton fibers from the seeds. For smooth operation of the processing machinery, and in order to optimize the quality of the cotton fiber whilst minimizing output wastage, it is necessary to control the moisture of the cotton fibers during the ginning process. Specifically, cotton fibers having too high a moisture content tend to cling to the processing machinery and form wads which decompose during storage. On the other hand, cotton fibers having too low a moisture content cling to metal surfaces as a result of static electricity generated on the fibers. Furthermore, as the moisture content of the cotton fibers is lowered, their strength is reduced resulting in more frequent breakage of the fibers. As a result, the effective throughput of the processing plant is reduced.

The optimum moisture content of cotton fibers is from 6.5 to 8%. However, depending on the period during the cotton harvest, cotton may arrive at the gins with a moisture content from less than 4% to more than 12%. For these reasons, steps must be taken, during the ginning process, either to reduce the moisture content of the cotton fibers or, alternatively, to increase it in order that the resulting moisture content may fall between the stated optimum limits. A moisture measuring device is thus an integral component of the moisture control system.

Cotton bales are massive structures typically having width of 0.5 m, a height of 0.7 m and a length of 1.4 m and a weight of 250 Kg±10%. Each bale typically comprises many layers which are bound together using metal bars. The moisture content through the bale may vary from one point to another by approximately 3%.

A moisture measuring device for measuring the moisture content of a cotton bale must be capable of processing one bale every 1.5–2 min for an average bale speed of approximately 1 ms$^{-1}$.

U.S. Pat. No. 4,578,998 describes a moisture content measuring system for sheet material which uses microwave radiation. Two pairs of microwave radiators and receivers are combined with surface and below surface temperature measuring sensors to furnish data to a computer which interprets the data and yields moisture readings. Each pair of microwave radiator and receiver straddles the sheet test material and checks microwave transmission through the material and reflected from it, but the two radiators are crossed-polarized so that signal interchange between then is avoided.

In such a system, the two radiators are cross-polarized to each other and one irradiates the bottom surface of the test material whilst the other irradiates the top. In fact, a pair of radiators and receivers are employed: one radiator being above the sheet material and the other below, the respective receivers being aligned with the radiators and, themselves, being disposed on opposite sides of the sheet material. In order to discriminate which radiated signal emanates from which radiator and to prevent cross-talk between the two radiators, the respective microwave signals in the two radiators are cross-polarized so that each receiver receives only the signal from its corresponding radiator. However, it is to be understood that the polarization of the signals, whilst being used for signal separation, is not actually employed to determine the moisture content of the sheet material. Furthermore, the system would not appear to be suitable for measuring the moisture content of multi-layer bales of material, such as cotton, having non-uniform moisture content through a section thereof.

Additionally, when measuring the moisture content of multi-layer bales of cotton, the results will vary according to whether the layers are parallel or not and it is therefore desirable to assess the extent to which the layers are parallel or not. No provision is made in U.S. Pat. No. 4,578,998 to achieve such an objective.

It will also be noted, particularly from the Figure and accompanying description of U.S. Pat. No. 4,578,998 that the respective radiators and receivers are disposed on either side of the sheet material in very close proximity thereto. Consequently, there is very little air between the respective radiators and receivers and therefore no compensation need be provided for the ambient moisture content of the air itself. However, owing to the massive structure of cotton bales, and the like, and their non-uniformity, there inevitably is a substantial air gap between the radiators and the receivers surrounding the cotton bale. Owing to the presence of this air gap, the resulting computation of the moisture content also includes the effect of any ambient moisture in the air surrounding the bale between the respective radiator and receiver. Unless this is compensated for, the resulting computation of the bale's moisture content will be inaccurate.

SUMMARY OF THE INVENTION

It is an object of the invention to provide a system for measuring the moisture content of a multi-layer bale of material, in which the drawbacks of hitherto proposed such systems are significantly reduced or eliminated.

According to a broad aspect of the invention, there is provided a system for measuring the moisture content of a multi-layer bale of material, the system comprising:

a source of microwave radiation disposed on a first side of the bale for directing a polarized source beam through the bale in a direction substantially parallel to the layers thereof so as to exit from the bale as an exit beam, conveyor means for conveying the bale past the source of microwave radiation, microwave antenna means disposed on an opposite side of the bale for receiving the exit beam, bale alignment means for determining when the bale is correctly aligned between the radiation source and the antennas and producing an alignment signal, amplitude determination means coupled to the microwave antenna means and to the bale alignment means and being responsive to said alignment signal for determining a maximum amplitude of the exit beam corresponding to an amplitude of the exit beam, attenuation determination means coupled to the amplitude determination means for determining an attenuation of the source beam, and moisture determination means coupled to the attenuation determination means and being responsive to said attenuation for determining the moisture content of the bale.

Preferably, a circularly polarized source beam is employed and is detected by a pair of cross-polarized antennas for receiving mutually orthogonal components of the exit beam. The moisture content associated with each of these components may then be determined after which a ratio may be calculated of the respective components of the moisture content in the two directions of the bale. It has been found that when the layers of the bale are parallel so that one component of the source beam is parallel to the layer structure and the other normal thereto, a characteristic ratio K is produced. Any difference between the measured ratio and the characteristic ratio K provides a measure of the deviation of the layer structure from the ideal parallel structure.

BRIEF DESCRIPTION OF THE DRAWINGS

In order to understand the invention and to see how the same may be carried out in practice, a preferred embodiment will now be described, by way of non-limiting example only, with reference to the accompanying drawings, in which.

DETAILED DESCRIPTION OF A PREFERRED EMBODIMENT

Figure 1:
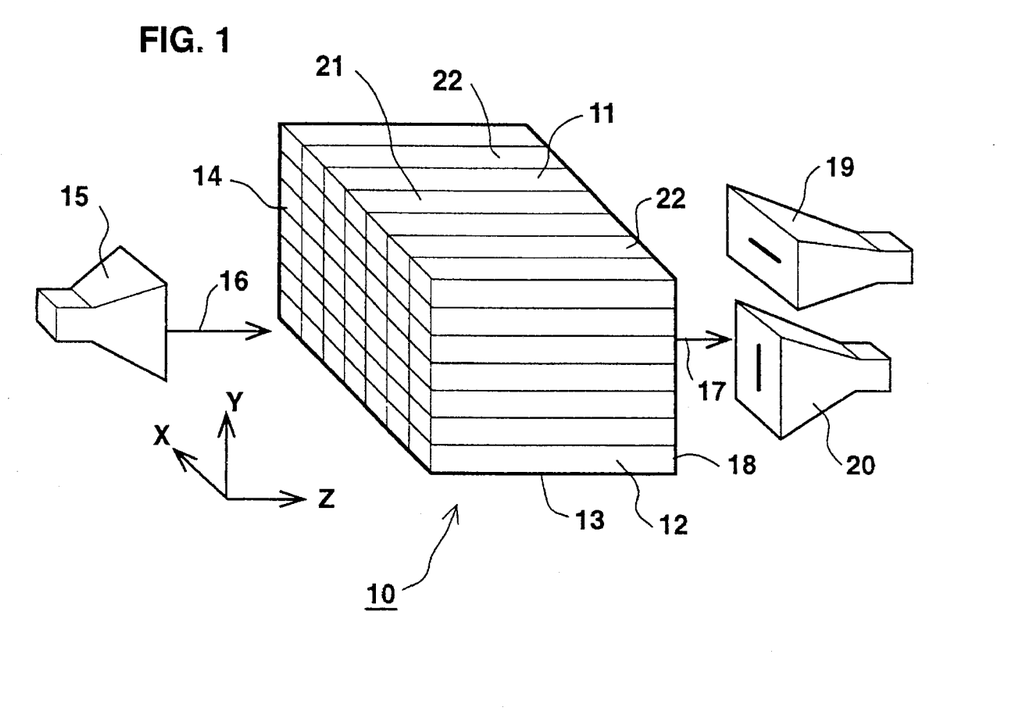
FIG. 1 shows pictorially a system according to the invention for measuring the moisture content of a multi-layer bale of cotton.

FIG. 1 shows part of a system 10 for measuring the moisture content of a multi-layer bale of material 11. The bale 11 has a plurality of layers 12 which, in the Figure, are substantially parallel to one another and to a base 13. At a first side 14 of the bale 11 there is disposed a source of microwave radiation 15 for directing a circularly polarized source beam 16 of microwave radiation having a frequency in the range 8 to 10 GHz in a direction substantially parallel to the layers 12 so as to exit from the bale 11 as a circularly polarized exit beam 17. For ease of reference, there is also shown in the Figure a Cartesian frame showing the directions of the respective X, Y and Z axes to which reference is made in the following description.

Disposed on a second side 18 of the bale 11 opposite the first side 14 thereof, there are disposed first and second microwave antennas 19 and 20 for receiving mutually orthogonal components of the exit beam 17. Throughout the measuring process, the bale 11 moves longitudinally along the X-axis so that each successive measurement actually relates to a slice 21 along the length of the bale 11. In order to prevent separation of the individual layers 12 within the bale 11, the bale 11 is bound at opposite ends thereof with metal straps or bars depicted as 22 which completely encircle the bale 11 and thus keep the layers 12 thereof intact.

Figure 2:
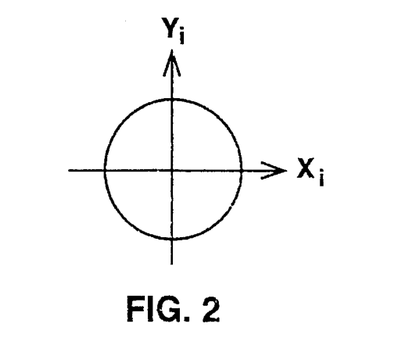
FIGS. 2 and 3 show schematically the amplitudes of circularly polarized input and output beams, respectively.
Figure 3:
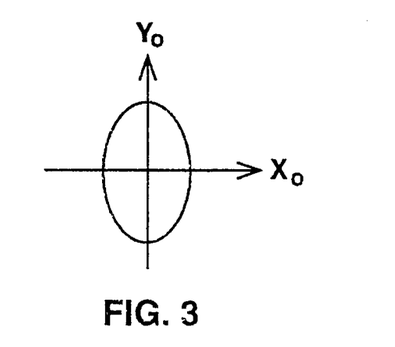

The source beam 16 is circularly polarized such that its respective components $X_i$ and $Y_i$ are equal in magnitude as shown in FIG. 2. With further reference to FIG. 1, it will be noted that the vertical component $Y_i$ of the source beam 16 passes through the bale 11 in a direction normal to the layers 12 whilst the horizontal component $X_i$ passes through the bale 11 in a direction parallel to the layers 12. As a result, the component $X_i$ of the source beam 16 encounters many more water molecules during its transition from the source 15 to the microwave antenna 19 than does the vertical component $Y_i$ of the source beam 16 during its corresponding transition. As a result, the horizontal component $X_i$ is attenuated to a much greater extent than the vertical component $Y_i$ and, as shown in FIG. 3, the resulting polar representation of the output beam is elliptical having its major axis in the vertical plane and its minor axis in the horizontal plane.

This is true for so long as the layers 12 of the bale are substantially parallel to the direction of the horizontal component $X_i$ of the source beam 16 such that its vertical component $Y_i$ is normal to the layer structure.

Figure 4:
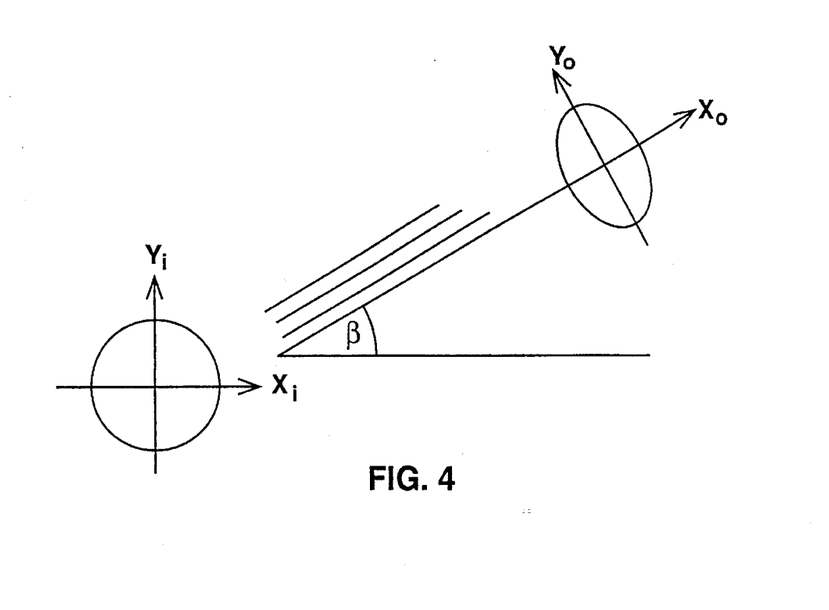
FIG. 4 shows schematically similar forms of the amplitudes when the layers are not parallel to the source beam such that the angle at which the output beam has a maximum amplitude is normal to the bale.

FIG. 4 shows the situation when this is no longer the case and the layer structure is inclined at an angle β to the horizontal component $X_i$ of the source beam 16. The resulting exit beam is still elliptically polarized but the major axis of the ellipse is tilted so as to be normal to the layer structure of the bale and the resulting maximal amplitude can be determined either by using a pair of microwave antennas as shown or, alternatively, by employing a single circularly polarized antenna.

Figure 5:
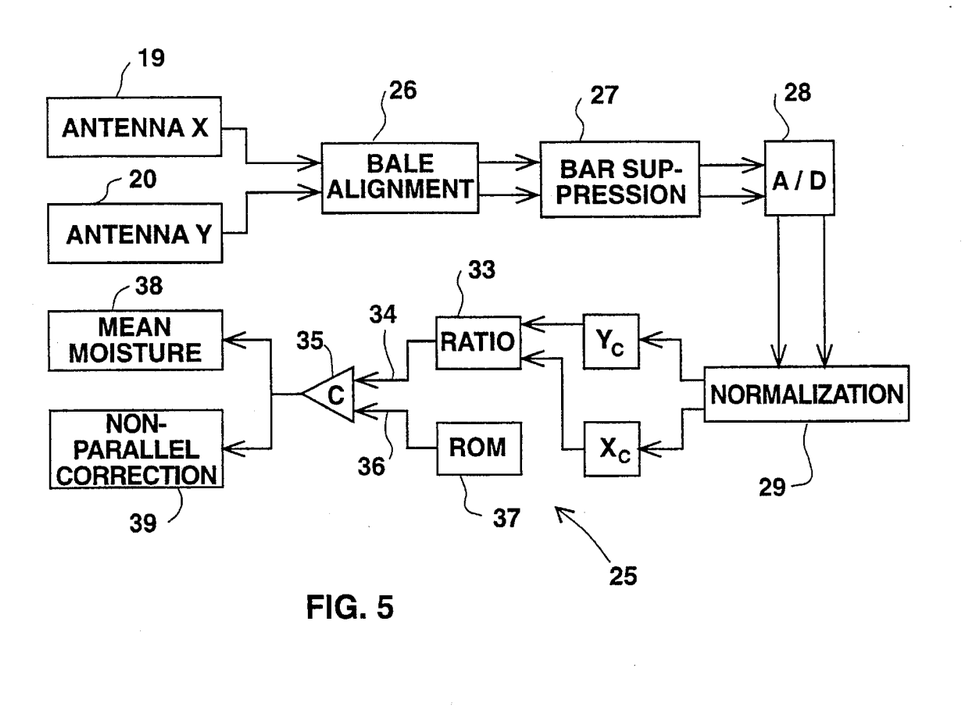
FIG. 5 is a block diagram showing functionally the principal components in a system according to the invention.

FIG. 5 shows the principal functional components of a moisture determination means 25 responsive to the respective signals received by the antennas 19 and 20. In fact, separate channels are connected to the antennas 19 and 20 so that their respective signals are processed separately. However, for the sake of simplicity, the components have not been duplicated in FIG. 5 but are represented as single blocks having dual inputs and outputs.

Thus connected to each of the antennas 19 and 20 are respective bale alignment means 26 for producing an alignment signal when the bale 11 is correctly aligned between the radiation source 15 and the antennas 19 and 20. The effect of the tie bars 22 is removed from the resulting signal by means of a bar suppression means 27 and the resulting analog signal is digitized by means of an analog-to-digital (A/D) converter 28. The resulting digital signal is normalized by a normalization unit 29 so as to compensate for the temperature, mass, length and material content of the bale 11. Specifically, denoting:

$Wx_i$=the $i^{th}$ moisture measurement in the X-channel, $Wy_i$=the $i^{th}$ moisture measurement in the Y-channel, $W_o$=the nominal mass of the bale≈250 Kg, $W_c$=the actual measured mass of the bale, $L_o$=the nominal length of the layers taken along the width of the bale, $L_c$=the actual length of the layers taken along the width of the bale, $T_o$=the base temperature of the cotton fibers (35° C.) and $T_c$=the temperature of the cotton fibers in the current slice, it may be shown that:

$$W_{x_i'} = \frac{T_o - T_c}{10}$$

$$W_{y_i'} = \frac{T_o - T_c}{10}$$

$$W_{x_i''} = W_{x_i'} \cdot \left(\frac{W_o}{W_c}\right)$$

$$W_{y_i''} = W_{y_i'} \cdot \left(\frac{W_o}{W_c}\right)$$

$$W_{x_i'''} = W_{x_i''} \cdot \left(\frac{L_o}{L_c}\right)$$

$$W_{y_i'''} = W_{y_i''} \cdot \left(\frac{L_o}{L_c}\right)$$

By means of corresponding normalization in both the X and Y channels, corresponding look-up tables may be computerized so as to permit the normalized values simply to be read off from the signals fed by the A/D converter 28 to the normalization unit 29 so as to produce corresponding corrected values $W_{i_x}$ and $W_{y_i}$ representing moisture content in the respective X and Y directions of a slice 21 of the bale 11. In the particular case that the layers 12 of the bale 11 are located substantially parallel to the X axis, the resulting bale is said to be "normal" and the total moisture concentration may be completely characterized by the moisture measurements provided by the X-channel, i.e. in that direction wherein the source beam 16 passes parallel to the layers 12 of the bale 11 and is thus subjected to the greater attenuation. However, if as shown schematically in FIG. 4, the layers 12 are not parallel to the X-axis, then the moisture measurements provided by the X-channel will not themselves characterize the true moisture concentration along the layers of the bale and a suitable correction factor must be provided so as to allow for the relative inclination of the bale's layers 12.

Such correction is provided by a ratio determination unit 33 which calculates the ratio $W_{i_x}:W_{i_y}$ being the normalized signals in the respective X and Y channels. It may be shown, empirically, that if the ratio is substantially equal to a predetermined coefficient K which, for cotton bales, may be 80, then the total moisture concentration of the current equal to the concentration $M_{i_x}$ along the X direction. However, any slice 21 in the bale 11 may be considered, to all intents and purposes, to be deviation of the calculated ratio from the predetermined coefficient K, is indicative of the layers 11 being non-parallel to the X direction such that the vector components of the source beam must be resolved in directions parallel and normal to the layers 11, as follows:

$$W_{i_{x(meas)}} = W_{i_x}\cos\beta + W_{i_y}\sin\beta$$

$$W_{i_{y(meas)}} = W_{i_x}\sin\beta + W_{i_y}\cos\beta$$

$$K = \frac{W_{i_x}}{W_{i_y}}$$

where:

$W_{i_{x(meas)}}$ = measured moisture content in the X direction for the $i^{th}$ slice, $W_{i_{y(meas)}}$ = measured moisture content in the Y direction for the $i^{th}$ slice, $W_{i_x}$ = maximum moisture content of the $i^{th}$ slice in the X-direction, $W_{i_y}$ = maximum moisture content of the $i^{th}$ slice in the Y-direction, $\beta$ = the angle of inclination of the layers to the X-direction, K = the ratio of the maximum moisture values in the X and Y directions, and $\alpha_i$ = the measured ratio $W_{i_{x(meas)}} : W_{i_{y(meas)}}$.

Figure 5A:
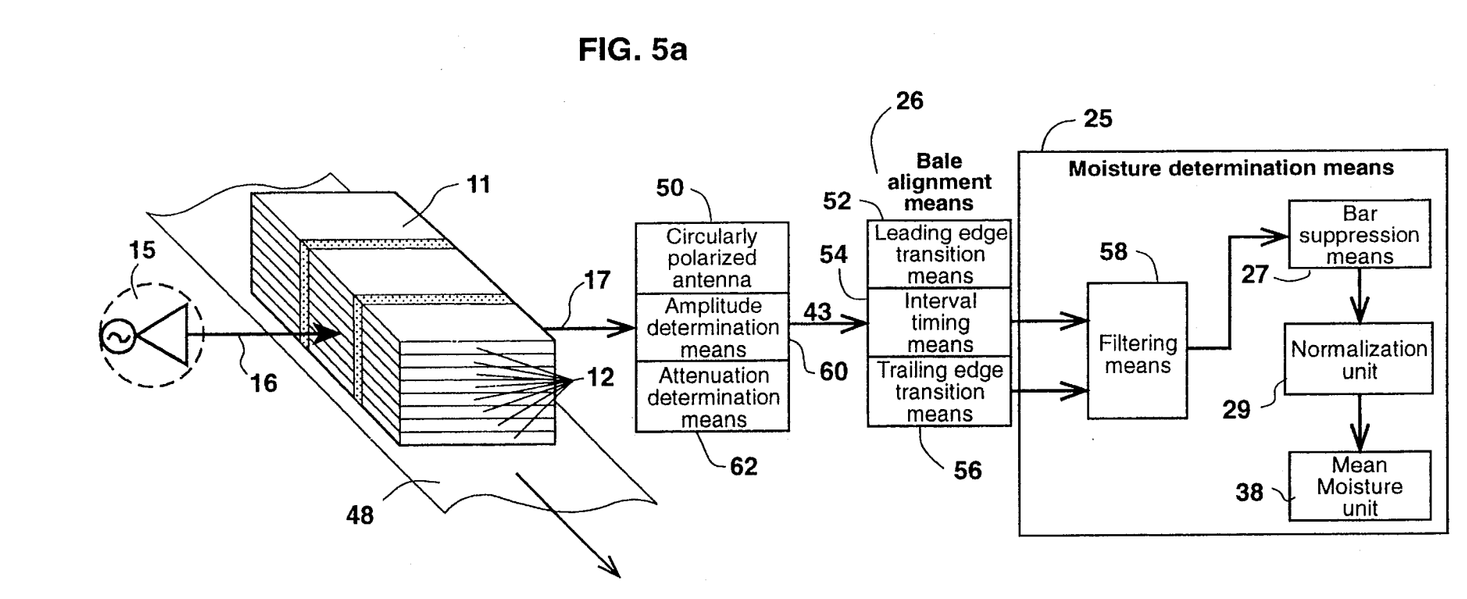
FIGS. 5A and 5B are block diagrams showing further components in a system according to the invention.

Thus, the ratio derived by the ratio determination unit 33 is fed to one input 34 of a comparator 35 having a second input to which the appropriate coefficient K is fed from a Read Only Memory (ROM) 37. Depending on the output of the comparator 35 being substantially equal to or greater than one, the moisture concentration of the bale is determined directly by a mean moisture unit 38 or by means of the correction function in accordance with the equations described above. FIG. 5A is a schematic illustration of system 10. A source of microwave radiation 15 produces a beam of microwave radiation 16. Beam 16 is received by at least one antenna 50, which is a circularly polarized antenna. Antenna 50 then produces an antenna signal 43. A conveyor means 48 moves bale 11 between source of microwave radiation 15 and antenna 50, such that beam 16 passes through a portion of bale 11, and exits bale 11 as an exit beam 17. Exit beam 17 is received by microwave antenna 50, producing an antenna signal 43.

Antenna signal 43 is then examined by a bale alignment means 26. Bale alignment means 26 then determines the alignment of bale 11 relative to source beam 16 and antenna 50. Bale alignment means 26 includes a leading edge transition means 52, an interval timing means 54 and a trailing edge transition means 56. Leading edge transition means 52 detects when a leading edge of bale 11 has passed source 15, and produces a leading edge transition signal. Interval timing means 54 receives leading edge transition signal and produces an alignment signal, such that the alignment signal is produced when the bale is correctly aligned between source 15 and antenna 50. Trailing edge transition means 56 determines when the trailing edge of bale 11 passes source 15, and produces a trailing edge transition signal.

A moisture determination means 25 then determines the moisture content of bale 11 from the alignment signal. Moisture determination means 25 determines an ambient moisture content after receiving the trailing edge transition signal. Moisture determination means 25 also includes a filtering means 58 for producing a corrected signal by removing the ambient moisture content from the alignment signal.

Antenna 50 can optionally include an amplitude determination means 60 and an attenuation determination means 62. Amplitude determination means 60 determines an amplitude of exit beam 17. Attenuation determination means 62 then produces an attenuated signal, by determining an attenuation of exit beam 17 from the amplitude of exit beam 17. The attenuated antenna signal is then processed in a similar fashion as antenna signal 43.

Figure 5B:
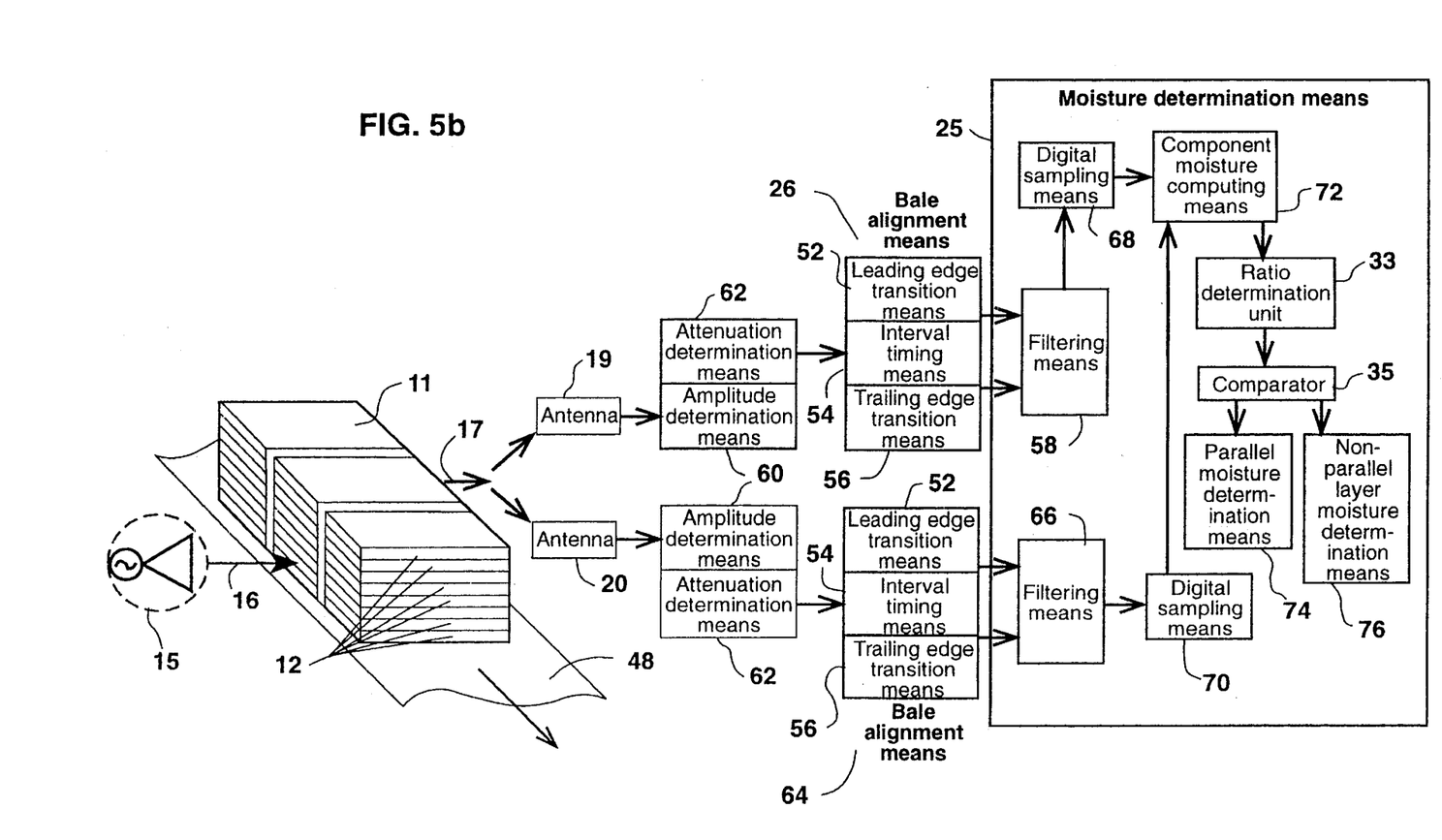

In the preferred embodiment shown in FIG. 5B, beam 16 is circularly polarized, and exit beam 17 has two mutually orthogonal components, each of which is received by one of two linearly polarized microwave antennas 19 and 20, respectively. Each mutually orthogonal component is separately processed, similar to the above description in FIG. 5A, so that there are two bale alignment means 26 and 64. Moisture determination means 25 has two filtering means 58 and 66 for removing the ambient moisture component and producing a corrected signal. Preferably, two digital sampling means 68 and 70 then produce a digitized signal from each component of the corrected signal. There is also preferably a component moisture computing means 72 which then computes a moisture content of each mutually orthogonal component of the digitized signal.

Preferably, moisture determination means 25 also has a ratio determination means 33 for determining a ratio of each of the moisture contents produced by component moisture computing means 72; a comparator 35 for comparing the ratio with a predetermined constant, the predetermined constant being obtained when the layers in bale 11 are substantially parallel; a parallel layer moisture determination means 74 for determining the moisture content of bale 11 when the ratio is substantially equal to the predetermined constant; and a non-parallel layer moisture determination means 76 for determining the moisture content of bale 11 when the ratio is substantially not equal to the predetermined constant.

Figure 6:
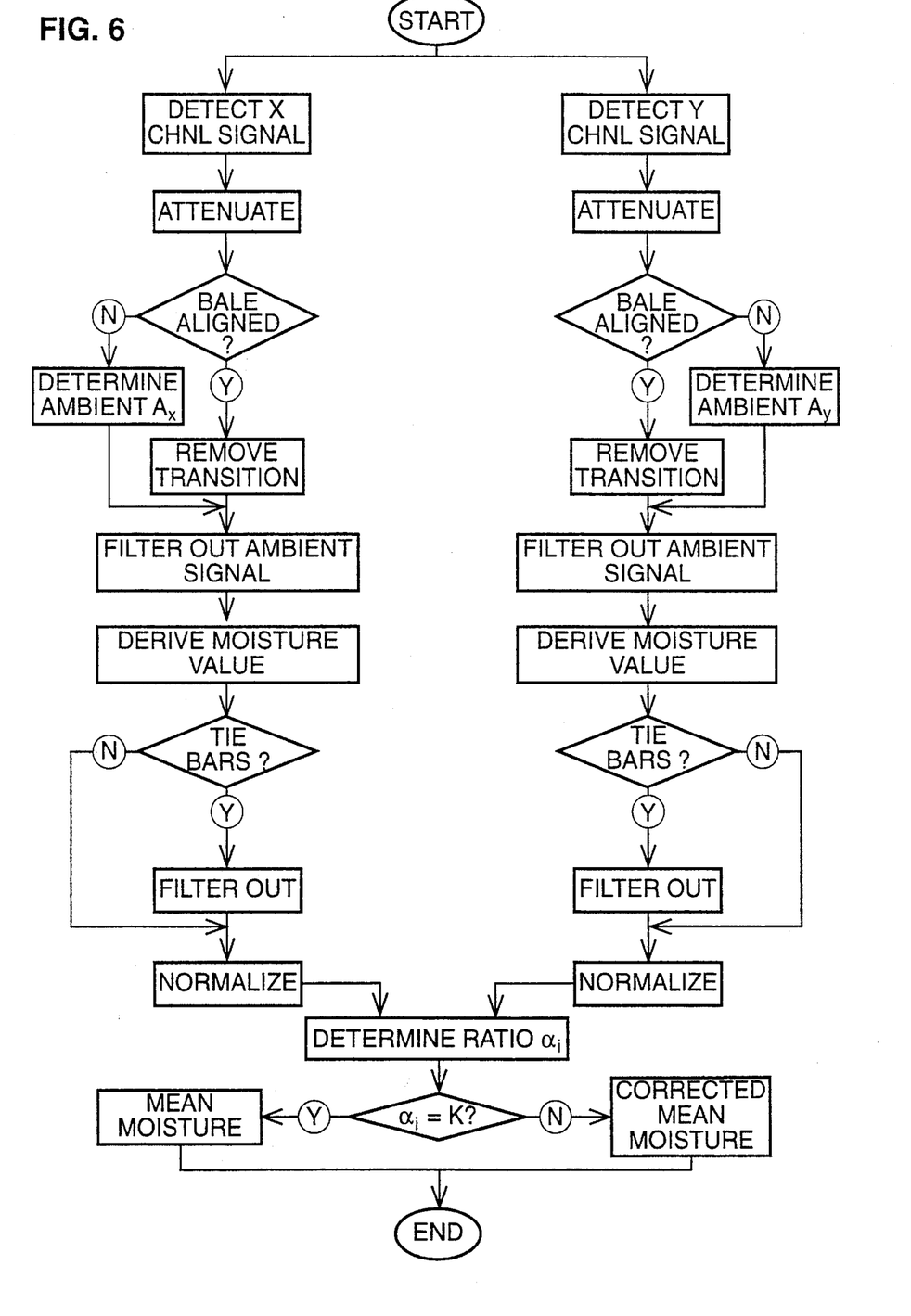
FIG. 6 is a flow diagram showing the principal method steps associated with the system of FIG. 5.

FIG. 6 is a flow diagram which summarizes the above-described determination of the bale's moisture content. Thus, at the outset of the process, respective signals are received by the antennas in each of the X and Y channels. If the bale is aligned between the source and receiving antennas, then the edge transition signal of the bales is removed from the resulting signal so that only the steady-state is considered in the subsequent processing. When the bale is well clear of the source and receiving antennas, the system determines the moisture content of the ambient air and, as will be explained below, this is then filtered out from the corresponding signals produced when a bale is aligned between the source and receiving antennas so as to correct for the moisture content of air surrounding the bale.

As explained above, successive measurements are taken for respective slices along the length of the bale as it is conveyed past the source and receiving antennas. The resulting successive signals are processed so as to eliminate therefrom the effects of the tie bars 22 shown in FIG. 1 which, being non-absorbent, have a very much lower attenuation than the absorbent cotton fibers. The resulting signals are normalized and the ratio of the normalized signals is then calculated. If the resulting normalized ratio equals the predetermined coefficient K, then the results of the Y-channel alone are sufficient for determining the average moisture content of the bale. Otherwise, the mean moisture content $W_i$ associated with the $i^{th}$ slice must be corrected using the normalized X-channel signal, according to the empirical function $f(\alpha_i, W_{i_x}, W_{i_y})$ where:

$$W_i = W_{i_{y(meas)}} 3.2 \times 10^{-2} \left( \frac{\alpha_i}{K} - 1 \right)$$

The attenuation in dB may be determined by the function:

$$A = 10 \, lg_{10} \left( \frac{P_{exit}}{P_{source}} \right)$$

where $P_{exit}$ and $P_{source}$ are the powers of the exit and source beams, respectively.

Figure 7:
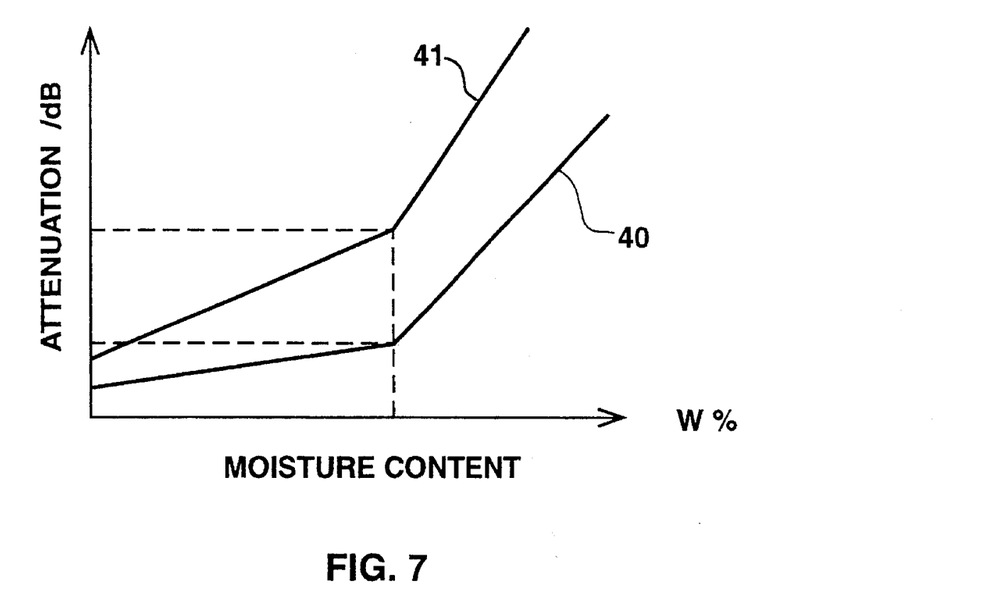
FIG. 7 shows graphically an empirical relationship between signal attenuation and moisture content.

Having thus determined the attenuation of the X and Y components of the source beam, the resulting moisture content of the bale may be determined empirically from a graphical relationship of the kind shown in FIG. 7 where two approximated curves 40 and 41 are represented for the directions Y and X, respectively. In fact, as shown in dotted outline in FIG. 7, the two curves may be shown to be parabolic functions, although their exact derivation is not itself a feature of the present invention. A more complete description of these curves and their derivation for a single direction may be found in "*Theoretical and Experimental Investigation of Microwave Moisture Measurement of Materials*" by A. Greenwald, "FAN", Uzbekistan, 1982.

As explained above, it is important to take the measurements only during that period of time when the bale 11 is correctly aligned between the source and receiving antennas. In fact, regardless of whether a bale is aligned between the antennas or not, a signal is always received by the receiving antennas for so long as the source antenna radiates the source beam.

Figure 8:
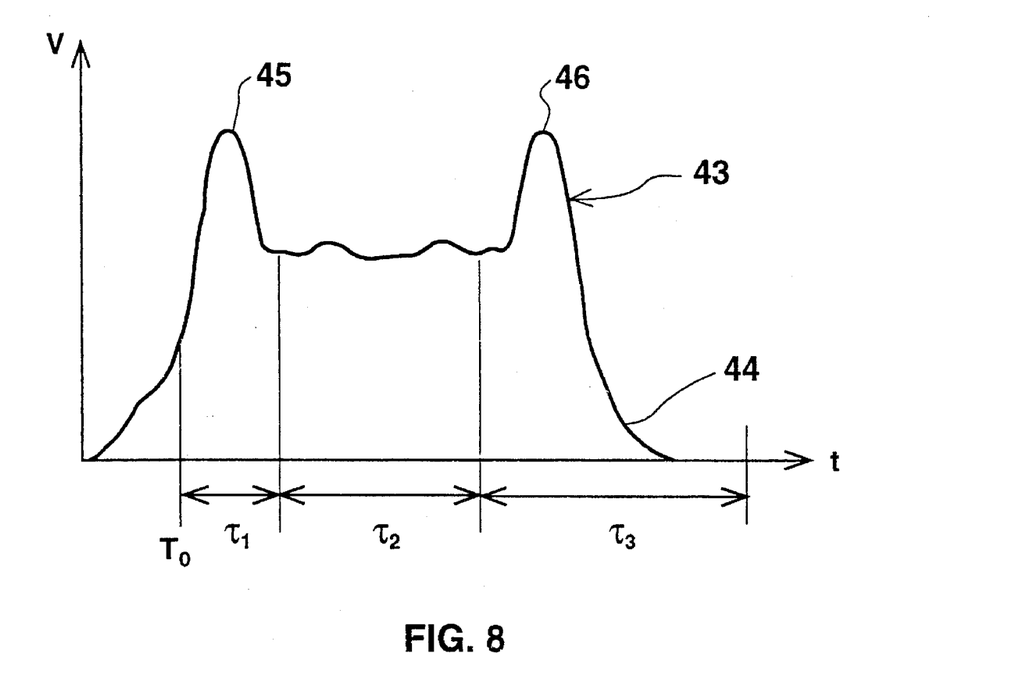
FIG. 8 shows graphically an exit signal received by the microwave antennas having associated therewith three distinct time periods $\tau_1$, $\tau_2$ and $\tau_3$.

FIG. 8 shows schematically a representation of the signal 43 received by the receiving antennas corresponding to a generally low background level 44 which climbs to an initial higher level at a time $T_0$ when a bale enters the region between the source antenna and the receiving antennas. Thereafter, the signal climbs producing a transient peak 45 owing to edge transition effects and settles down after a time interval $\tau_1$ to a generally stable level representative of the moisture content of the bale. Throughout the time interval $\tau_2$ the signal remains substantially constant subject to minor fluctuations owing to local inequalities in the bale's moisture content until, at the end of the second time interval $\tau_2$, the trailing edge of the bale starts to emerge past the source and receiving antennas thereby giving a second local peak 46 whereafter, after a third time interval $\tau_3$, the bale has completely cleared the gap between the source and receiving antennas such that the resulting signal is representative of the ambient moisture concentration.

Although the invention has been described with particular reference to the use of a circularly polarized beam employing two receiving antennas for receiving mutually orthogonal components of the exit beam, a single circularly polarized detector can be employed instead which permits the maximum amplitude of the exit beam to be determined regardless of the inclination of the major axis of the elliptical output beam.

In the preferred embodiment, the source beam is circularly polarized and is directed in a direction substantially parallel to the layers of the bale. However, if desired the source beam may be linearly polarized and directed in a direction substantially normal to the layers of the bale. Likewise, the microwave antenna means may be either a circularly polarized antenna or may include two linearly polarized antennas having mutually orthogonal directions of polarization.

It will further be appreciated that, although in the preferred embodiment the bale alignment means is responsive to the exit beam for determining when the bale is correctly aligned between the radiation source and the antennas, other alignment means may be employed without derogating from the principles of the invention. For example, optical means may be employed to located the position of the bale relative to the radiation source and antennas so as to produce the required alignment signal.

We claim:

1. A device for measuring the moisture content of a multi-layer bale of material, comprising:
    (a) a source of microwave radiation for producing a microwave radiation source beam;
    (b) at least one microwave antenna for receiving an exit beam and for producing an antenna signal, said exit beam being said source beam after a transition from said source to said antenna, said at least one microwave antenna being located substantially opposite said source of microwave radiation;
    (c) a conveyor means for conveying the bale between said source of microwave radiation and said at least one microwave antenna, such that when said source beam passes through a portion of the bale, said exit beam is received by said antenna, and such that said source beam is enabled to pass through a plurality of portions of the bale;
    (d) a bale alignment means, for examining said antenna signal and determining the alignment of the bale relative to said antenna and said source of microwave radiation, said bale alignment means including:

(i) a leading edge transition means, for detecting when a leading edge of the bale passes said source of microwave radiation and producing a leading edge transition signal after said leading edge has passed said source of microwave radiation;

(ii) an interval timing means, for producing an alignment signal after receiving said leading edge transition signal, said alignment signal being said antenna signal produced during a time interval when the bale is correctly aligned between said source of microwave radiation and said antenna; and (iii) a trailing edge transition means, for detecting when a trailing edge of the bale passes said source of microwave radiation and producing a trailing edge transition signal after said trailing edge has passed said source of microwave radiation; and (e) a moisture determination means for determining the moisture content of the bale from said alignment signal and for determining an ambient moisture content after receiving said trailing edge transition signal, said moisture determination means including:

(i) a filtering means for producing a corrected signal by removing said ambient moisture content from said alignment signal; and (ii) a mean moisture unit for computing the moisture content of the bale from said corrected signal.

2. The device of claim 1, wherein said moisture determination means further includes a normalization unit for normalizing said corrected signal and producing a. normalized signal, and said mean moisture unit computes the moisture content of the bale from said normalized signal.

3. The device of claim 2, wherein said antenna further includes:

(a) an amplitude determination means for determining an amplitude of said exit beam; and (b) an attenuation determination means for determining an attenuation of said exit beam from said amplitude, such that said antenna signal is an attenuated signal.

4. The device of claim 3, wherein the bale includes at least one tie bar, and said moisture determination means further includes a bar suppression means for removing an effect caused by said source beam contacting said tie bar from said corrected signal and for producing a further corrected signal.

5. The device of claim 3, further including a curve for comparing said normalized signal to said curve, and for determining a moisture content from said curve.

6. The device of claim 2, wherein said source beam is circularly polarized, and said source beam is substantially parallel to the layers of material.

7. The device of claim 2, wherein said source beam is linearly polarized, and said source beam is substantially normal to the layers of material.

8. The device of claim 6, wherein said at least one microwave antenna is a circularly polarized antenna.

9. The device of claim 6, wherein said antenna is two linearly polarized antennas for receiving two mutually orthogonal components of said beam and producing an antenna signal with two mutually orthogonal components.

10. The device of claim 9, wherein each of said antennas further includes an amplitude determination means for determining an amplitude of one of said mutually orthogonal components of said exit beam, and an attenuation determination means for determining an attenuation of one of said mutually orthogonal components of said source beam from said amplitude, such that said antenna signal is an attenuated signal.

11. The device of claim 9, wherein said moisture determination means further includes:

(a) two digital sampling means for producing a digitized signal from each component of said corrected signal;

(b) a component moisture computing means for computing a moisture content from each of said mutually orthogonal components of said digitized signal;

(c) a ratio determination unit for determining a ratio of said moisture contents;

(d) a comparator for comparing said ratio with a predetermined constant K, said predetermined constant being obtained when the layers in the bale are substantially parallel;

(e) a parallel layer moisture determination means for determining the moisture content of the bale when said ratio is substantially equal to said predetermined constant;

(f) a non-parallel layer moisture determination means for determining the moisture content of the bale when said ratio is substantially not equal to said predetermined constant.

12. The device of claim 11, wherein said non-parallel layer moisture determination means determines said moisture content of the bale by using an empirical function $$W = W_y + 3.2 \times 10^{-2} \frac{(\alpha - 1)}{K}$$

W being said moisture content of said signal, $W_y$ being said moisture content of one of said mutually orthogonal components, said component having passed through the bale in a direction normal to the layers, $\alpha$ being said ratio, and K being said predetermined constant.

13. A method of determining the moisture content of a bale of material with multiple layers and a tie bar, comprising:

(a) producing a circularly polarized microwave radiation beam;

(b) receiving said source beam as an exit beam with two linearly polarized antennas;

(c) conveying the bale between said microwave radiation source and said microwave antenna, such that when said source beam passes through a portion of the bale, said exit beam is received by said microwave antenna, and such that said source beam is enabled to pass through a plurality of portions of the bale;

(d) determining an amplitude of each mutually orthogonal component of said exit beam;

(e) determining an attenuation of each of said mutually orthogonal components from said amplitude and producing an attenuated signal;

(f) determining an alignment of the bale relative to said source of microwave radiation and said antenna, and then alternately producing one of three signals:

(i) a leading edge transition signal, after a leading edge of the bale passes said source of microwave radiation;

(ii) an alignment signal, after receiving said leading edge transition signal, said alignment signal being said antenna signal during a time interval when the bale is correctly aligned between said source of microwave radiation and said bale; and (iii) a trailing edge transition signal, after a trailing edge of the bale passes said source of microwave radiation;

(g) determining a moisture content of ambient air signal after receiving said trailing edge transition signal;

(h) filtering said moisture content of ambient air signal from said alignment signal, producing a corrected signal;

(i) removing an effect of said source beam contacting the tie bar from said corrected signal, producing a further corrected signal;

(j) normalizing said further corrected signal, so that a normalized signal is produced;

(k) determining a moisture content of each of said mutually orthogonal components of said normalized signal by comparing said normalized signal to a calibration curve;

(l) calculating a ratio of said moisture contents;

(m) comparing said ratio to a predetermined constant; and (n) alternately computing a moisture content of the bale directly from said normalized signal, when said ratio is substantially equal to said predetermined constant, and computing a corrected moisture content of the bale when said ratio is not substantially equal to said predetermined constant.

* * * * *